(12) United States Patent
Bowman et al.

(10) Patent No.: US 9,724,020 B2
(45) Date of Patent: Aug. 8, 2017

(54) APPARATUS AND METHOD FOR ADAPTING A PIEZOELECTRIC RESPIRATORY SENSING BELT TO A RESPIRATORY INDUCTANCE PLETHYSMOGRAPHY POLYSOMNOGRAPH

(71) Applicant: DYMEDIX CORPORATION, Shoreview, MN (US)

(72) Inventors: Bruce R. Bowman, Eden Prairie, MN (US); Allen J. Pickard, Minnetonka, MN (US); Peter Stasz, Mounds View, MN (US)

(73) Assignee: Dymedix Corporation, Shoreview, MN (US)

(*) Notice: Subject to any disclaimer, the term of this patent is extended or adjusted under 35 U.S.C. 154(b) by 685 days.

(21) Appl. No.: 14/268,429

(22) Filed: May 2, 2014

(65) Prior Publication Data
US 2014/0330156 A1   Nov. 6, 2014

Related U.S. Application Data

(60) Provisional application No. 61/819,122, filed on May 3, 2013.

(51) Int. Cl.
*A61B 5/08* (2006.01)
*A61B 5/113* (2006.01)
*A61B 5/00* (2006.01)

(52) U.S. Cl.
CPC .......... *A61B 5/1135* (2013.01); *A61B 5/4806* (2013.01); *A61B 5/6831* (2013.01)

(58) Field of Classification Search
CPC .......... A61B 5/113; A61B 5/00; A61B 5/1135; A61B 5/4806; A61B 5/6831
See application file for complete search history.

(56) References Cited

U.S. PATENT DOCUMENTS

| | | | |
|---|---|---|---|
| 6,011,992 A * | 1/2000 | Hubbard | A61B 5/05 600/535 |
| 6,254,545 B1 | 7/2001 | Stasz et al. | |
| 6,491,642 B1 | 12/2002 | Stasz | |
| 6,702,755 B1 * | 3/2004 | Stasz | A61B 5/0878 600/534 |
| 2008/0275356 A1 | 11/2008 | Stasz et al. | |

(Continued)

*Primary Examiner* — Navin Natnithithadha
*Assistant Examiner* — Eric Messersmith
(74) *Attorney, Agent, or Firm* — Nikolai & Mersereau, P.A.; Thomas J. Nikolai

(57) ABSTRACT

Circuits for rendering piezo-based respiratory belts compatible with polysomnograph (PSG) machines designed for use with respiratory induction belts (RIPs) comprise an instrumentation amplifier adapted to be connected to a piezoelectric transducer and providing an AC output signal to a low-pass filter. In a first embodiment, the low-pass filter output is applied to an input of a microcontroller's A to D converter and the resulting digitized samples are used to vary the resistance of a digital potentiometer whose wiper terminal is coupled in series with an inductor so as to emulate the presence of a RIP belt to the PSG machine. In a second embodiment, the low-pass filter output is used to drive the primary of a transformer so as to vary the permeability of the transformer's ferrite core in a way that emulates the performance of a RIP belt to the PSG.

10 Claims, 3 Drawing Sheets

(56) References Cited

U.S. PATENT DOCUMENTS

2009/0259135 A1* 10/2009 Stasz .................... A61B 5/7214
  600/534
2009/0264784 A1 10/2009 Stasz

* cited by examiner

APPARATUS AND METHOD FOR ADAPTING A PIEZOELECTRIC RESPIRATORY SENSING BELT TO A RESPIRATORY INDUCTANCE PLETHYSMOGRAPHY POLYSOMNOGRAPH

CROSS REFERENCE TO RELATED APPLICATION

The present application claims priority to provisional application Ser. No. 61/819,122 filed May 3, 2013.

BACKGROUND OF THE INVENTION

I. Field of the Invention

This invention relates generally to polysomnograhy (PSG) and more particularly to improved respiratory excursion sensing belts and an associated adapter that allows the improved sensing belts to be used with respiratory inductance plethysmography (RIP) based PSG machines. It bridges two incompatible technologies, piezoelectric (a high impedance capacitive output voltage due to stressing of a PVDF film) and low impedance inductor (which has its inductance changed when the RIP belt is stretched).

II. Description of the Prior Art

In a polysomnographic study, a variety of physiologic parameters must be measured. One of the most important assessments, breathing, is obtained by measurement of nasal and/or oral airflow in tandem with measurements of chest and abdominal wall movement.

An important task in securing and interpreting a polysomnogram is to assess whether apnea is present and to distinguish between obstructive and central apnea. Obstructive apnea is defined as an absence of airflow in the presence of continued effort to breathe. While this is a fairly straightforward definition, physiological assessment of obstructive apnea can be challenging. The essential task is to demonstrate effort to breathe in the absence of significant airflow.

Respiratory effort is directly measured by esophageal manometry. Esophageal pressure (Pes) is measured by having the patient swallow a pressure catheter which then resides in the esophagus throughout the sleep study. Rhythmic fluctuations in thoracic pressure in the absence of significant nasal and oral airflow are the best "proof" of the presence of obstructive apnea. In clinical practice, however, esophageal pressure is bothersome to most patients and is therefore not used routinely. A reasonable surrogate measure of respiratory effort can be obtained by measuring changes in chest and/or abdominal volume, also known as plethysmography. Changes in lung volume are most accurately measured using spirometry equipment, in which lung volumes and flow rates are determined by having the patient breathe through a pneumotachograph, and are unsuitable for polysomnography.

There are three primary methods of non-invasive chest and abdominal plethysmography in current use: measurement of changes in elastic belt tension, measurement of changes in transthoracic electrical impedance and measurement of changes in electrical inductance.

An elastic belt fastened around the chest or abdomen will exhibit a change in tension as the chest or abdomen expands or contracts. This change in tension can be easily measured and converted to a voltage by a variety of methods. The most common method in current use is a piezoelectric sensor, i.e., a crystal that directly generates a voltage when compressed or stretched. This method, while simple and inexpensive, is subject to trapping artifacts where a portion of an elastic belt becomes "trapped" as a person turns from one side to another during sleep, resulting in variable tension along the belt circumference. As a result, this method can both significantly under and/or overestimate the actual degree of chest or abdominal movement in addition to creating a false signal when the belt tension suddenly changes with a change in body position.

In the case of impedance plethysmography, the human body is a fairly poor conductor of electricity. It presents a fairly high impedance to electrical current flowing through it. This impedance changes as the cross-section of the body expands and contracts, allowing qualitative measurement of thoracic and abdominal movement during breathing. A plurality of electrodes are attached to the skin. A weak alternating current is passed through these electrodes, allowing the impedance to be measured. This method yields a non-linear signal, thus is useful only as a qualitative measurement of chest or abdominal movement. In addition, this signal is prone to movement artifact and cardiac artifact that can present challenges in discerning when the signal actually represents chest wall contraction or expansion due to breathing effort.

Respiratory inductance plethysmography (RIP) relies on the principle that a current applied through a loop of wire generates a magnetic field normal to the orientation of the loop (Faraday's Law) and that a change in the area enclosed by the loop creates an opposing current within the loop directly proportional to the change in the area (Lenz's Law). An elastic belt into which a zigzagging (coiled) wire is sewn is worn around the chest or abdomen. An alternating current is passed through the belt, generating a magnetic field. The frequency of the alternating current is set to be much greater than the typical respiratory rate in order to achieve adequate sampling of the respiratory effort waveform and in order to monitor the change in inductance due to breathing reliably. The act of breathing changes the cross-sectional area of the patient's body, and thus changes the shape of the magnetic field generated by the belt, inducing an opposing current that can be measured, most easily as a change in the frequency of the applied current. The signal produced is linear and is a fairly accurate representation of the change in cross-sectional area. In addition, RIP does not rely on belt tension, thus is not affected by belt trapping.

The American Academy of Sleep Medicine (AASM) has generally recommended the use of inductive sensing belts for measuring abdominal and thoracic circumferential changes due to respiration. These elastic belts incorporate an elongated, stretchable bent wire embedded therein that is driven by an oscillator whose frequency varies with inductance changes due to stretching and relaxing of the belts during breathing. It relies upon the self inductance and mutual inductance properties of the wires and their embedding in a stretchable belt.

Problems due to undetected wire breakage have resulted in aborted PSG procedures so frequently that the inductive belts are falling out of favor with many sleep lab professionals. An alternative respiratory belt is based on the piezoelectric properties of polyvinylidene fluoride (PVDF) films. An example of a respiratory belt based on PVDF technology is described in published U.S. patent application 2008/0275356, the contents of which are hereby incorporated by reference as if fully set forth herein.

While PVDF based respiratory belts produce a robust signal output linearly proportional to the elongation changes, they tend not to be directly compatible with all PSG machines that have been designed to accommodate RIP belts. This has inhibited the market acceptance of PVDF based respiratory belts.

It is accordingly an object of the present invention to provide an adapter circuit that will accept the piezo signal from a PVDF film transducer in a respiratory belt and produce an output that emulates that produced by RIP belts so that the PVDF belt can be used with existing PSG machines already ubiquitously present in the field.

SUMMARY OF THE INVENTION

The adapter of the present invention comprises an instrumentation amplifier stage connected to receive the piezo signal from the belt and amplify that signal while removing common made noise before it is applied to a low-pass filter, preferably a third order Butterworth filter having unity gain and a cutoff frequency of approximately 0.5 Hz. The filter removes certain motion and other artifacts from the signal.

The processed signal is then applied to a further circuit that functions to generate an inductance equivalent to that which a PSG designed to work with RIP expects to see.

DESCRIPTION OF THE DRAWINGS

The foregoing features and advantages of the invention will become apparent to persons skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

This description of the preferred embodiments is intended to be read in connection with the accompanying drawings, which are to be considered part of the entire written description of this invention. Terms such as "connected", "connecting", "attached", "attaching", "join" and "joining" are used interchangeably and refer to one structure or surface being secured to another structure or surface or integrally fabricated in one piece, unless expressively described otherwise.

Figure 1:
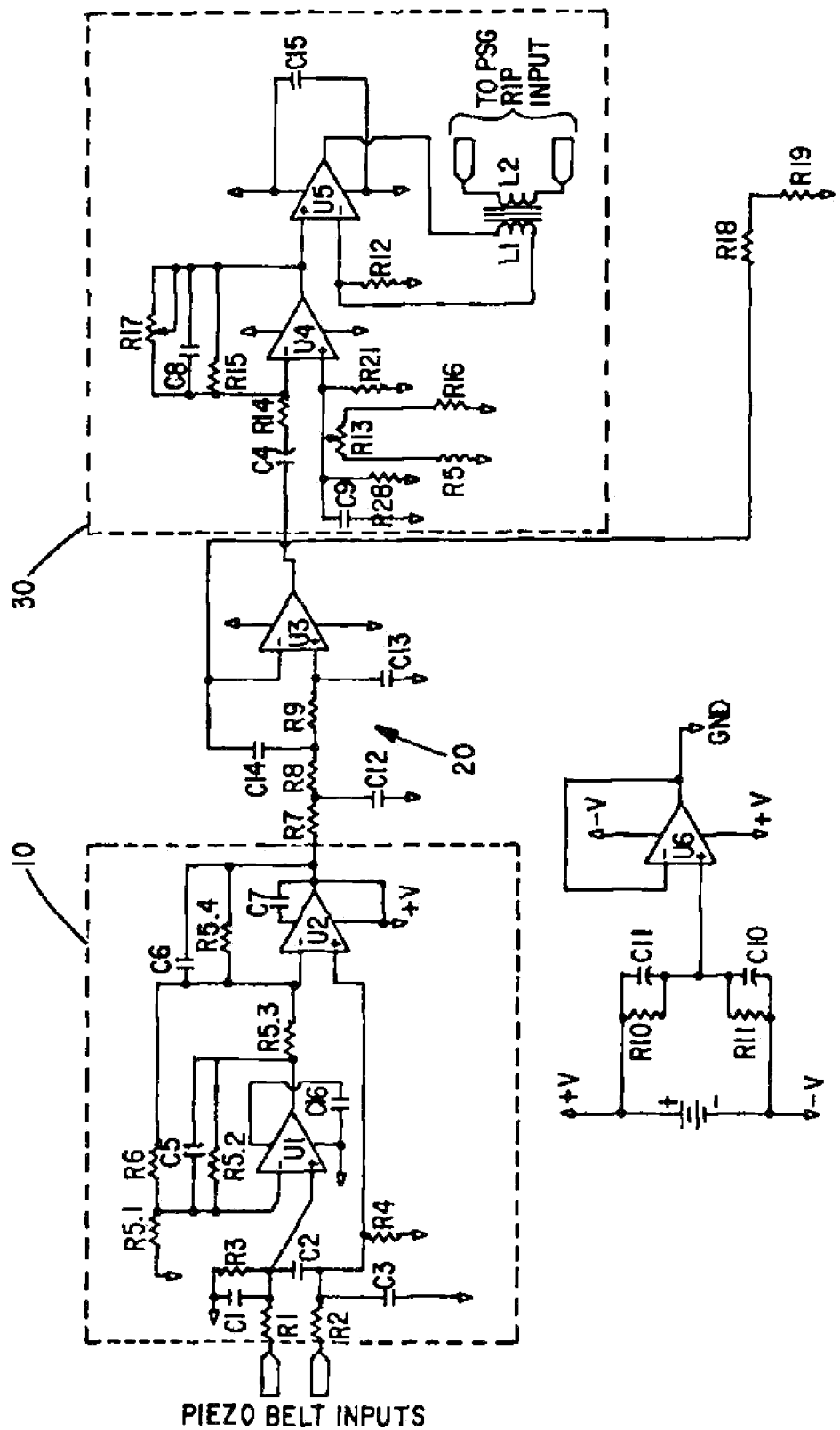
FIG. 1 is a schematic electrical diagram of a circuit for adapting a signal output from a piezo (PVDF) based transducer to an output device originally designed to work with an inductive respiratory belt.

Referring first to FIG. 1, enclosed by the dashed line box 10, it is an instrumentation amplifier comprising op amps U1 and U2 which receive as inputs a voltage signal generated by a piezoelectric PVDF film embodied in a belt that is adapted to encircle the chest or abdomen of a sleep study patient and expand and contract with a person's breathing. The instrumentation amplifier 10 functions to increase the common-mode noise rejection of the adapter system, making it less susceptible to 60 Hz noise present in the environment. Without limitation, the amplifier 10 may have a gain in the range of from 2 to 10 with approximately 6.4 being preferred.

The output from the amplifier stage 10 is applied to a third order Butterworth low-pass filter 20. While a third order Butterworth low-pass filter is preferred, those skilled in the art will appreciate that other types of low-pass filters known in the art may also be employed. In the present embodiment, the cut-off for the filter 20 may be about 0.5 Hz although a workable range may extend that by an order of magnitude greater. The filter is included to remove unwanted artifacts. The instrumentation amplifier and filter combination may be the same as described in U.S. Pat. No. 6,702,755 which is incorporated by reference herein.

The amplified and filtered piezo signal is a low frequency (less than 1 Hz) signal and it is then applied to a network designed to convert the piezo-based signal to one that effectively emulates the inductance of a RIP-type belt so that the PSG generates a signal similar to that if it were being used with a RIP belt. The belt inductance of a RIP-type belt runs anywhere from around 2 to 8 microhenries with an additional approximately 15 microhenries in the clasp that electrically engage the belt in the case of one RIP belt manufacturer. A function of the circuit surrounded by the broken line box 30 is to introduce an appropriate inductance or inductive reactance value consistent with RIP belt technology. The signal that gets processed into the inductance equivalent that the RIP-type PSG expects to see is conditional by the operational amplifier's U4 and U5. Op amp U4 is simply an amplifier with an offset capability to establish a linearity region in which a RIP belt normally operates. In the circuit of FIG. 1 there is included a variable resistor $R_{13}$ which along with resistors $R_5$ and $R_{16}$ form a voltage divider that creates an offset adjustment capability for the amplifier U4. If no offset is found necessary, capacitor $C_9$ can be shorted out and $R_5$, $R_{13}$, $R_{16}$, $R_{20}$ and $R_{21}$ can be removed. If an offset is needed at the output of U4 then $C_9$ is left in place and $R_5$, $R_{16}$ and $R_{13}$ are replaced with fixed resistors $R_{20}$ and $R_{21}$ that produce the same DC offset voltage at the output of U4 as obtained when $R_5$, $R_{16}$ and $R_{13}$ were in place.

The belt inductance found in most commercially available RIP style belts runs anywhere from around 2 microhenries to an 8.2 microhenries, depending upon the manufacturer. It was found through experiments that the signal that appears at the inductor that goes to the RIP head box has to be modulated so as to be equivalent to the change experienced when a RIP belt expands and contracts with breathing. To replicate that, there is provided a transformer coupling labeled L1 for the primary winding and L2 to the secondary winding disposed on a ferrite core. The secondary winding L2 mimics the inductance that the associated PSG expects to see. Winding L1 not only couples a voltage (frequency less that 1 Hz) into L2, but more basically, the signal driving it changes the permeability of the ferrite core such that winding L2 produces the equivalent of an inductance change of an RIP belt.

Windings L1, L2 are preferably wound on a bobbin having two halves such as an EP13 produced and sold by Ferroxcube International Holding B.V. Winding L2 has been established experimentally to represent what the PSG wants to perceive as the equivalent inductance of a RIP belt, even though the time varying signals are derived from the piezo properties of PVDF film material.

As previously explained, the circuit 30 of FIG. 1 produces a change of inductance due to the stretching and relaxation of the elastic belt incorporating PVDF film by appropriately modulating the permeability of the core of the inductors L2 which, in turn, produces the variation of inductance that the RIP based PSG box expects.

Summarizing, the piezoelectric signals coming from the abdominal and thoracic belt PVDF transducers is either a low frequency (less than 5 Hz) voltage or the current signal that gets processed by the instrumentation amplifier comprising op amps U1 and U2 and the low-pass filter provided by U3. The drive signal from the PSG headbox that normally activates the RIP belt is of a high frequency of 100 kHz to 500 kHz (typical depending on the inductance of the system it is driving). This same high frequency signal drives the inductance of the L1/L2 ferrite core inductors. Circuitry in the PSG machine monitors the voltage change to the high frequency drive signal from the PSG resulting from the inductance change caused by the permeability shifts precipitated by the modulation of core permeability due to the piezo signal. As a result, the PSG machine sees a similar signal as that seen when a RIP belt is attached and being stretched by breathing.

To comply with the teaching requirements of 35 U.S.C. §112, presented below is a list of component values that may be employed in creating an operable embodiment of the circuit of FIG. 1. These values are not to be considered as the only ones that result in an operable embodiment, however.

| Resistors | Capacitors | Other |
|---|---|---|
| $R_1$, $R_2$, $R_6$ = 49.9k | $C_1$, $C_3$ = 100 pf | $U_1$-$U_6$ = MCP 6041 |
| $R_3$, $R_4$ = 51.1M | $C_2$ = .001 µf | $L_2$-2.2 µH |
| $R_{5.1}$-$R_{5.4}$ = 100K | $C_4$ = 10 µf/Tant | |
| $R_{12}$ = 499 | $C_7$ = .01 µf | |
| $R_{13}$ = 100K pot | $C_8$, $C_9$ = 0.1 µf | |
| $R_{14}$-$R_{16}$ = 1M | $C_{10}$, $C_{11}$ = 1 µf/Tant | |
| $R_{17}$ = 1M pot | $C_{12}$ = 0.39 µf | |
| $R_{18}$ = 150K | $C_{13}$ = 0.056 µf | |
| $R_{19}$ = 1.8K | $C_{14}$ = 1 µf | |
| $R_{20}$-$R_{21}$ = 1M | $C_{15}$ = 0.01 µf | |

Figure 2A:
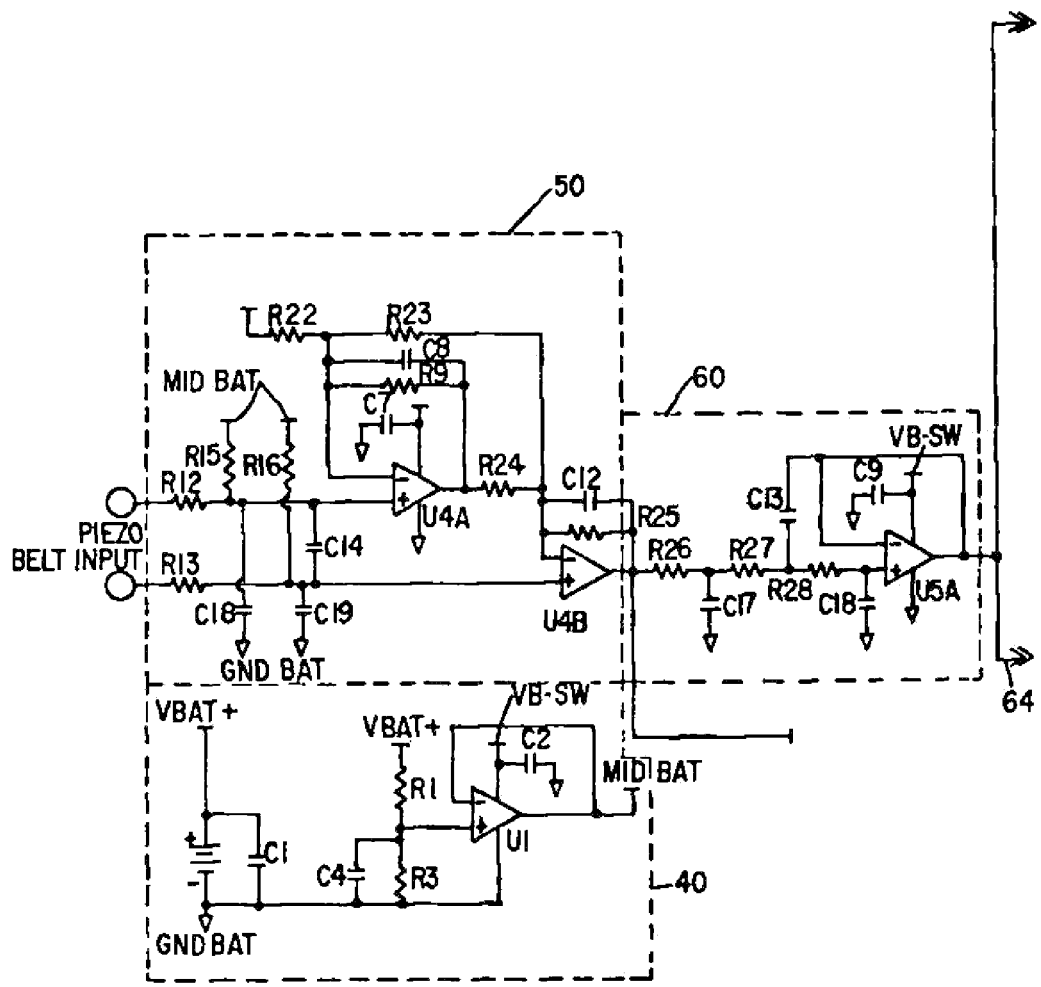
FIGS. 2A and 2B comprise a schematic electrical diagram of an alternative preferred embodiment of the present invention.
Figure 2B:
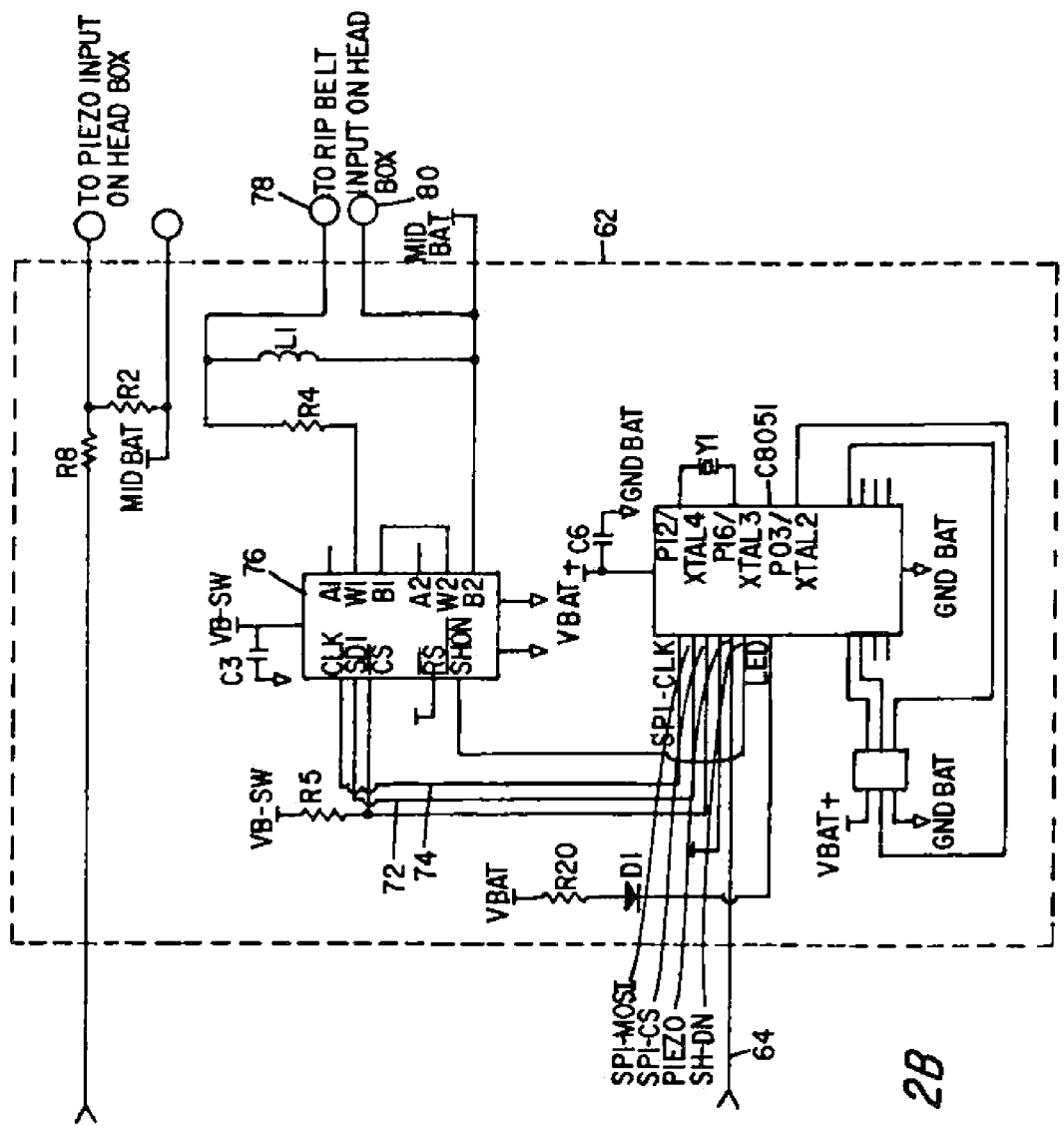

Turning next to FIG. 2, there is shown an alternative embodiment of the present invention for adapting PVDF transducer respiratory belts to RIP polysomnographic machines. In the circuit of FIG. 2, the broken line box 40 encloses the power supply source used to develop the operating potentials for the remainder of the circuitry of FIG. 2. The broken line box 50 encloses an instrumentation amplifier that amplifies the difference between two input signals comprising the output from the PVDF film transducer mounted on a body encircling belt. The instrumentation amplifier further serves to reject any signals that are common to both inputs. It therefore provides the important function of extracting small signals from the PVDF transducer. In addition to providing common mode rejection, it provides bandwidth sufficient for the present application.

As in the embodiment of FIG. 1, the output from the instrumentation amplifier 50 is applied to the input of a low-pass filter, here shown enclosed by broken line box 60. Again, it has been found that a third order Butterworth low-pass filter is admirably suited to the present application in that it affords a flat frequency response in the pass band where here it is designed to have a cutoff frequency of 0.5 Hz.

Focusing on the circuitry contained within the dashed line box 62, the signal processed analog piezo signal derived from a respiratory belt is applied over a conductor 64 as an input to a C8051F998 integrated circuit microcontroller and more particularly to its on-chip successive approximation register (SAR) analog-to-digital converter, all of which is more particularly described in data sheets for the C8051F998 microcontroller, copyright 2010 by Silicon Laboratories. The digitized values of the periodically sampled analog piezo input signal are first applied to a look-up table in the microcontroller and the resulting digitized samples are sent over a serial data input bus 72 clocked by timing signals on the serial clock input line 74 to an AD8402 digital potentiometer 76.

In the embodiment of FIG. 2, variable inductance is achieved by varying the amount of resistance that is connected in parallel with a fixed inductor identified in the schematic diagram of FIG. 2 by reference L1. The value of the fixed inductor is based upon that which is expected to be seen by the PSG involved. The amount of variation in inductance required is quite small—on the order of 0.15% of the fixed inductance L1. Varying the resistance in a range of approximately 600 ohms to 1660 ohms provides the necessary range of net inductance. It is the function of the digital potentiometer 76 to supply this variation in resistance. A 1 k-ohm digital potentiometer has a residual wiper resistance of typically 200 ohms, and an additional external resistor $R_4$ is wired in series with the potentiometer to yield the desired range.

In that the relationship between parallel resistance and net inductance is found not to be linear, a look-up table is incorporated in the C8051F998 microcontroller. The values in the look-up table have been calculated based upon the assumption that the desired inductance change should have a linear relationship with the analog input voltage from the Butterworth filter network 60.

Resistance in series with the inductor L1 results in a phase shift at lower frequencies, and resistance in parallel with the inductor results in phase shift at higher frequencies, so these parameters must be controlled properly to achieve the desired response in the frequency range in which the PSG machine operates. One PSG system used in testing the embodiment of FIG. 2 was found to operate in the frequency range of approximately 100 Khz to 200 Khz. The series resistance of the inductor L1 was found to cause a phase shift of approximately 3 degrees at 100 Khz and will increase as the frequency decreases. The minimum parallel resistance of the circuit is approximately 630 ohms, which will cause a phase shift of approximately 3 degrees at 200 Khz and will increase as the frequency increases. The variable inductance output at terminals 78, 80 are connected to a RIP input of a PSG machine, with the result being a valid breathing wave form being presented on the PSG monitor screen.

In implementing the invention of FIG. 2, the following component values were found to result in an operative embodiment.

| Resistors | Capacitors | Other |
|---|---|---|
| $R_1$, $R_3$, $R_{15}$, $R_{16}$ = 5.1M | $C_1$ = 47 µf | $U_1$ = MCP6041 |
| $R_4$ = 432 Ω | $C_2$, $C_4$, $C_6$, $C_7$, $C_9$, | $U_3$ = C8051F998 |
| $R_5$, $R_9$, $R_{24}$, $R_{25}$ = 100K | $C_{15}$ = 0.1 µf | U4, U5 = MCP6042 |
| $R_{12}$, $R_{13}$ = 200K | $C_3$ = 10 µf | Digital Potentiometer = |
| $R_{20}$ = 2K | $C_8$ = 100 pf | AD8402 |
| $R_{21}$ = 1.8K | $C_{12}$ = 1000 µf | $L_1$ = 18 µH |
| $R_{23}$ = 49.9K | $C_{14}$ = .033 µf | |
| $R_{26}$ = 1M | $C_{16}$ = .056 µf | |
| | $C_{17}$ = 0.39 µf | |
| | $C_{18}$, $C_{19}$ = 100 pf | |

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A circuit interfacing a polyvinylidene fluoride (PVDF) piezoelectric transducer to a respiratory inductance (RIP) input to a polysomnograph machine comprising:
   a) a PVDF transducer adapted to be applied to a patient for sensing respiratory activity and producing a voltage output signal proportional to the respiratory activity;
   b) an instrumentation amplifier having an input coupled to receive said voltage output signal from the PVDF transducer and operative to reduce common mode noise in said voltage output signal, said instrumentation amplifier having an output feeding a low-pass filter stage; and
   c) means coupled to an output from said low-pass filter stage for modulating an inductance element to produce an input signal compatible with a RIP machine.

2. The circuit of claim 1 wherein the PVDF transducer is affixed to an elastic belt adapted to surround the torso of the patient proximate at least one of his or her chest and abdomen.

3. The circuit of claim 1 wherein the instrumentation amplifier produces a gain in a range of from 2 to 10.

4. The circuit of claim 1 wherein the instrumentation amplifier produces a gain of about 6.4.

5. The circuit of claim 1 wherein the low-pass filter stage comprises a 3rd order Butterworth filter having a cut-off frequency in the range of from 0.5 Hz to 5 Hz.

6. The circuit of claim 1 wherein the means coupled to an output from the low-pass filter stage for modulating an inductance element comprises a programmable microcontroller having an analog-to-digital converter (ADC) that is coupled to receive the output from the low-pass filter stage and produce digital patterns representative of the amplitude of the output from the low-pass filter at discrete time intervals;
   a digital potentiometer coupled to receive said digital patterns and producing a resistance variation in relation to the digital patterns being received; and
   an inductor coupled to a wiper terminal of the digital potentiometer, said inductor having a nominal value corresponding to an inductance value presented to a RIP machine and changes from said nominal value being due to said resistance variations.

7. The circuit of claim 6 wherein the programmable microcontroller further comprises a look-up table for mapping ADC codes to said digital patterns.

8. The circuit of claim 6 and further including a fixed resistor serially connected between the wiper terminal and the inductor.

9. The circuit of claim 1 wherein the means coupled to an output from said low-pass filter stage for modulating an inductance element comprises: a first operational amplifier with its inverting input AC coupled to the low-pass filter output and an optional voltage divider coupled to the non-inverting input thereof and a second operational amplifier current driver connected to an output of the first operational amplifier and having an output connected to drive a primary winding of a ferrite core transformer and with a secondary winding of the transformer adapted for connection to RIP inputs of a PSG machine.

10. The circuit of claim 9 with said optional voltage divider removed.

* * * * *